(12) United States Patent
Wolcott

(10) Patent No.: US 6,499,362 B1
(45) Date of Patent: Dec. 31, 2002

(54) IN-LINE FILTER PROBE FOR PROCESS ANALYSIS

(75) Inventor: Duane K. Wolcott, Fox Island, WA (US)

(73) Assignee: Global FIA, Inc., Gig Harbor, WA (US)

( * ) Notice: Subject to any disclaimer, the term of this patent is extended or adjusted under 35 U.S.C. 154(b) by 0 days.

(21) Appl. No.: 09/683,222

(22) Filed: Dec. 3, 2001

(51) Int. Cl.[7] .................................................. G01N 1/00
(52) U.S. Cl. .................................................... 73/863.24
(58) Field of Search ....................... 73/863.01, 863.21, 73/863.23, 863.24, 863.31, 863.33, 863.81, 863.83, 863.84, 864.33, 864.81; 55/350.1, 482; 210/407, 409, 420, 424, 425, 510.1

(56) References Cited

U.S. PATENT DOCUMENTS

| | | | | |
|---|---|---|---|---|
| 3,685,345 A | * | 8/1972 | Wise ........................ | 73/863.21 |
| 4,501,161 A | * | 2/1985 | Endo et al. ............... | 73/863.24 |
| 4,529,521 A | | 7/1985 | Cortes ......................... | 210/635 |
| 4,775,476 A | | 10/1988 | Melcher et al. ............. | 210/635 |
| 4,779,466 A | * | 10/1988 | Ramsner et al. ......... | 73/863.24 |
| 4,921,607 A | * | 5/1990 | Langley | |
| 5,001,938 A | | 3/1991 | Downie .................... | 73/864.34 |
| 5,125,277 A | * | 6/1992 | Zievers | |
| 5,368,725 A | | 11/1994 | Bredeweg et al. .......... | 210/137 |
| 5,646,337 A | * | 7/1997 | Fonteyne .................. | 73/863.31 |
| 5,736,654 A | * | 4/1998 | Dubois ..................... | 73/863.84 |

* cited by examiner

Primary Examiner—Robert Raevis
(74) Attorney, Agent, or Firm—Reginald F. Roberts, Jr.

(57) ABSTRACT

An in-line filter probe for process analysis. The probe, which has a U-shaped porous tube mounted on a support and sealed at the tube's midsection, is placed in a process stream to provide filtered samples of the stream.

4 Claims, 7 Drawing Sheets

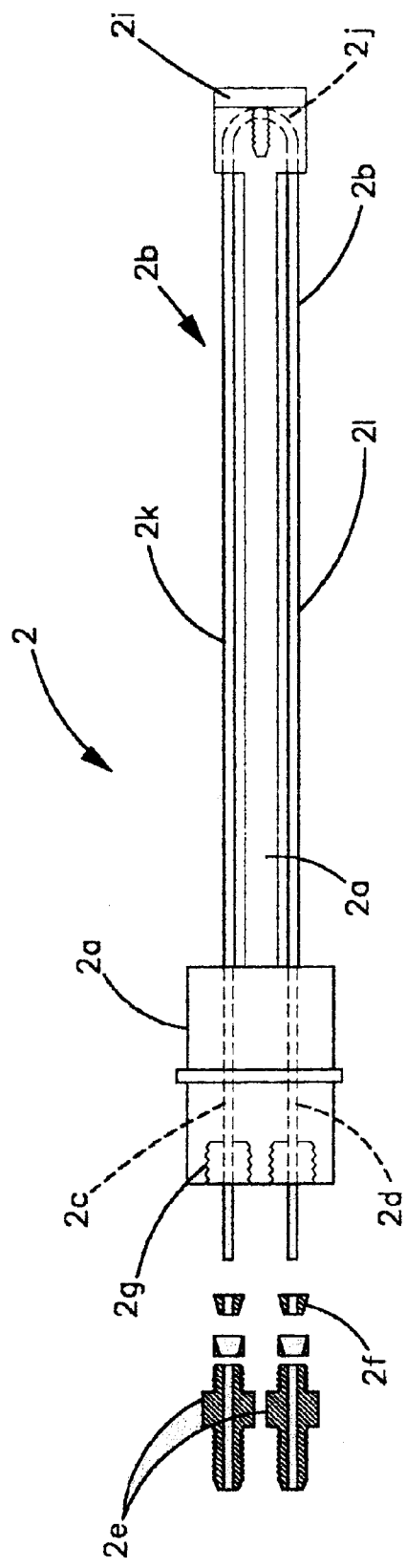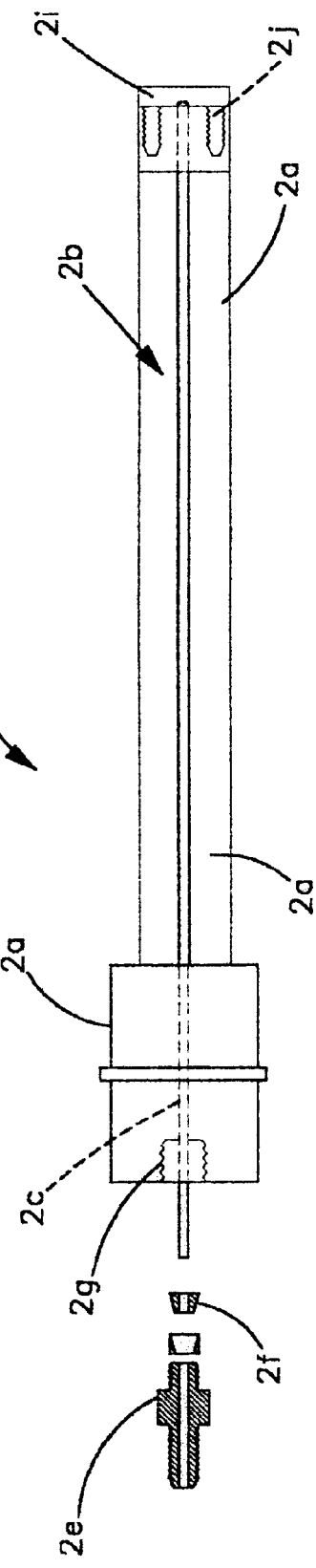

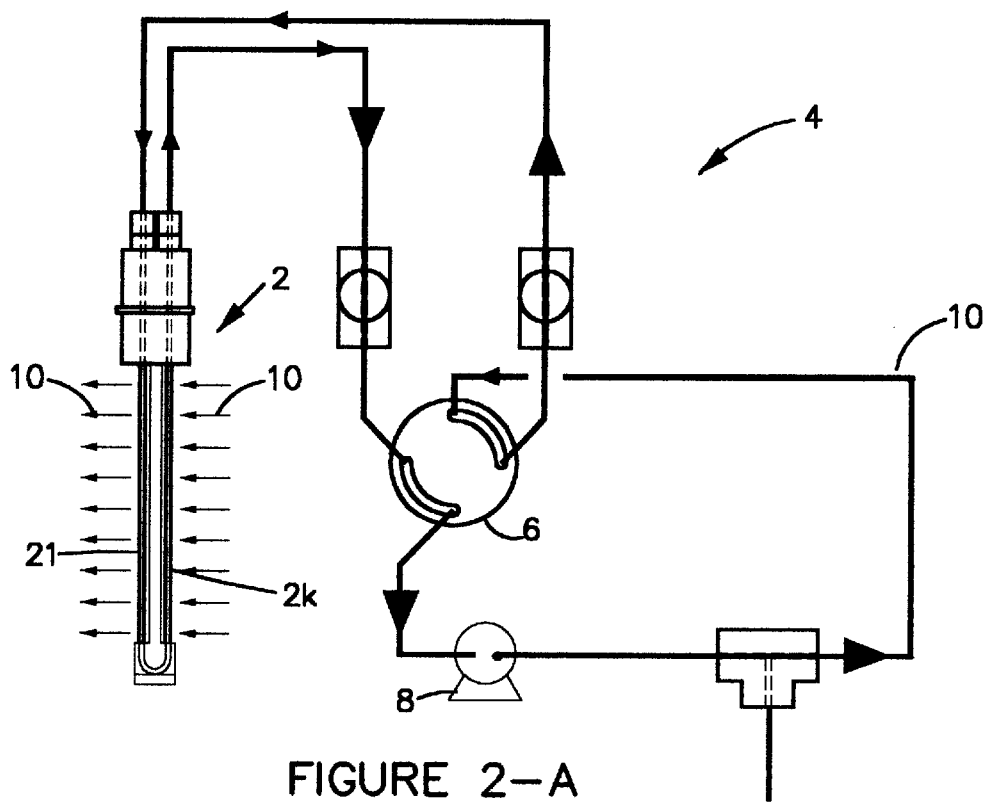
FIGURE 2-A
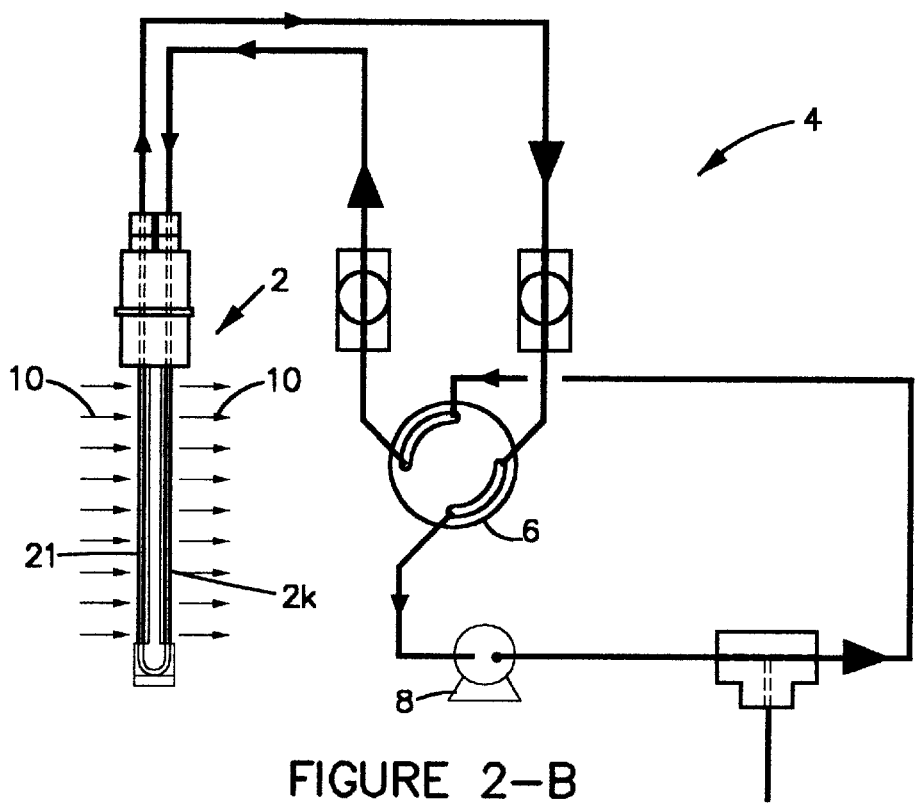
FIGURE 2-B

IN-LINE FILTER PROBE FOR PROCESS ANALYSIS

BACKGROUND OF INVENTION

The present invention relates to process analysis. More particularly, the invention relates to a sampling system for process analysis utilizing an in-line filter probe.

Sample cleanup for process analytical chemistry of liquid samples almost invariably involves a filtration step. Accomplishing such filtration is difficult, due to the need for extreme long-term reliability with minimal maintenance requirements.

The present invention provides a sampling system and corresponding methodology which accomplishes the task of sample filtration, protects the elements of the cleanup transport system, removes the absolute minimum amount of sample from the process, and provides the capability of automatically cleaning the filtration elements, thereby greatly reducing and possibly eliminating the need for manual cleaning and replacement of the filter elements.

SUMMARY OF INVENTION

In general, the present invention in a first aspect provides a sampling system for process analysis utilizing an in-line filter probe. The system comprises (a) a support element; (b) a first segment of porous tubing having an open first end and a closed second end, mounted on the support element; and (c) a second segment of porous tubing having an open first end and a closed second end, mounted on the support element.

In a second aspect the invention provides a method for fabricating an in-line filter probe. The method comprises (a) providing a support element; (b) mounting on the support element in a U-shaped configuration a porous tube open at first and second ends; and (c) sealing the tube between its first and second ends, thereby forming first and second open-ended segments connected to one another by a sealed third segment.

In a third aspect the invention provides a method for obtaining samples for process analysis utilizing an in-line filter probe. The method comprises (a) providing an in-line filter probe comprising a support element, a first segment of porous tubing having an open first end and a closed second end, mounted on the support element, and a second segment of porous tubing having an open first end and a closed second end, mounted on the support element; (b) disposing the filter probe in a fluid to be sampled; and (c) circulating the fluid through the porous tube.

BRIEF DESCRIPTION OF DRAWINGS

FIG. 1-A is a top view of an in-line filter probe made in accordance with the principles of the present invention.

FIG. 1-B is a side view of the in-line filter probe shown in FIG. 1-A.

FIGS. 2-A and 2-B are schematic representations of a first embodiment of a sampling system utilizing the in-line filter probe shown in FIGS. 1-A and 1-B, made in accordance with the principles of the present invention.

DETAILED DESCRIPTION

Figure 3:
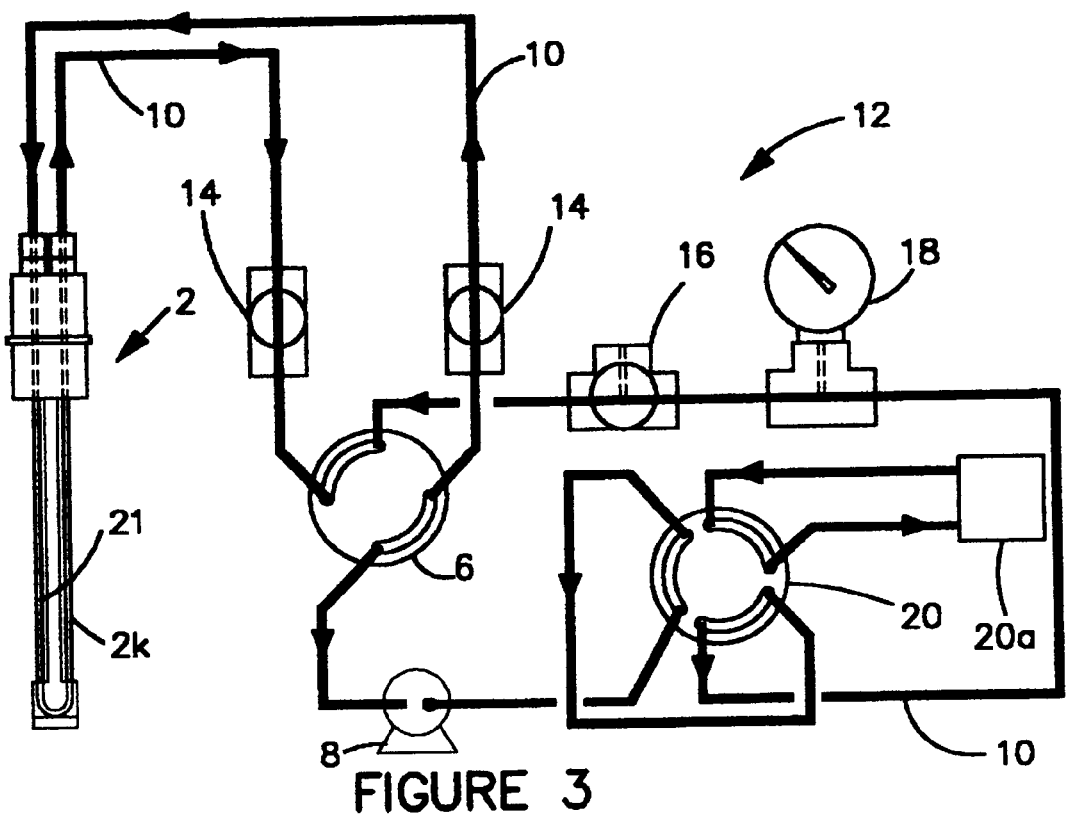
FIG. 3 is a schematic representation of a second embodiment of a sampling system utilizing the in-line filter probe shown in FIGS. 1-A and 1-B, made in accordance with the principles of the present invention.

More specifically, reference is made to FIGS. 1-A and 1-B, in which is shown an in-line filter probe, made in accordance with the principles of the present invention, and generally designated by the numeral 2. The in-line filter probe 2 comprises a support element 2a on which is mounted a U-shaped porous tube 2b. The tube 2b is preferably a single length of porous poly(tetrafluoroethylene) tubing having a porosity of about ten microns. The porosity or material of the tube 2b, however, may be changed as required or desired.

The filter tube 2b is anchored at its first and second open ends 2c and 2d by termination assembles 2e which form a leak-tight and physically strong grip on the ends 2c and 2d of the tube 2b when connected thereto by ferrules 2f and threaded ports 2g. The filter tube 2b is securely attached to the support element 2a by end cap 2i. The termination assemblies 2e are constructed and arranged to allow connection of transport tubing and fittings (not shown) to the ends 2c and 2d of the filter tube 2b.

After mounting, the end cap 2i is screwed into place to compress a segment 2j of the filter tube 2b, pinching it shut and isolating first and second separate filtration segments 2k and 2l. It is possible to use two separate filter tubes and/or other geometries of dual-element filtration devices to accomplish the objectives and carry out the functions disclosed herein, but the geometry shown in FIGS. 1-A and 1-B provides the most compact configuration possible, and is the preferred embodiment.

Reference is now made to FIGS. 2-A and 2-B, in which is shown a first embodiment of a sampling system utilizing the in-line filter probe 2, made in accordance with the principles of the present invention and generally designated by the numeral 4.

The filter probe 2 is installed as part of the sampling system 4, which adds to the filter probe 2a stream-switching valve 6 and a sample circulation pump 8. The stream-switching valve 6may be a single four or six-port valve plumbed up in a stream-switching configuration, or multiple three-way valves to perform the same function. A single four/six-port valve simplifies the necessary control-switching hardware (not shown). The circulation pump 8 may be of any type such as centrifugal, gear, or piston that provides the necessary motive force to drive sample fluid 70 through the sampling system 4, the direction of flow of the fluid 10 being indicated by arrows.

Referring now to FIG. 2-A, under process pressure and suction from the pump 8, process fluid 10 enters the first filtration segment 2k of the in-line filter probe 2. The fluid 10 then circulates through the stream-switching valve 6 and circulation pump 8, and under pressure from the pump 8 is forced back to and through the second filtration segment 2l. Particulate matter is removed from the circulating stream 10 by the first filtration segment 2k, so that the stream-switching valve 6 and pump 8 are exposed only to particle-free fluid, thereby minimizing wear and extending the operational life of the valve 6 and pump 8.

At some experimentally-determined optimum time, or by means of a triggering signal derived from pressure and/or flow sensors (not shown), the stream-switching valve 6 is automatically actuated. As shown in FIG. 2-B, the flow-path geometry of the fluid 10 is such that upon said actuation the direction of flow through the first and second filtration segments 2k and 2l is reversed, but the direction of flow through the pump 8 and valve 6 remains unidirectional. After flow reversal, the second filtration segment 2l becomes the inlet filtration segment, and the first filtration segment 2k the outlet filtration segment. Any particulate matter which has built up as a filter cake upon or deposited within the pores of the first filtration segment 2k is now flushed out by clear sample fluid 10 flowing in the reverse direction through the filtration segment 2k.

Reference is now made to FIG. 3, in which is shown a second embodiment of a sampling system utilizing the in-line filter probe 2, made in accordance with the principles of the present invention and generally designated by the numeral 12. The configuration shown in FIG. 3 discloses the application of the in-line filter probe 2 to analytical instrumentation such as a gas chromatograph, a high-pressure liquid chromatograph, a flow-injection analyzer, or other analytical instruments, utilizing injection valves for sample introduction.

The sampling system 12 comprises the filter probe 2, stream-switching valve 6, circulation pump 8, block valves 14, a three-way ball valve 16, a pressure gauge 18, and an injection valve 20 which introduces an intermittent sample to a flow-injection analyzer 20a.

The block valves 14, which are preferably operated manually, are disposed between and connect the stream-switching valve 6 and the porous tubing 2k, 2l to one another. The three-way block valve 16, disposed between and connecting the injection valve 20 and the flow-switching valve 6 to one another, provides means for a manual chemical or solvent backwash.

Figure 4:
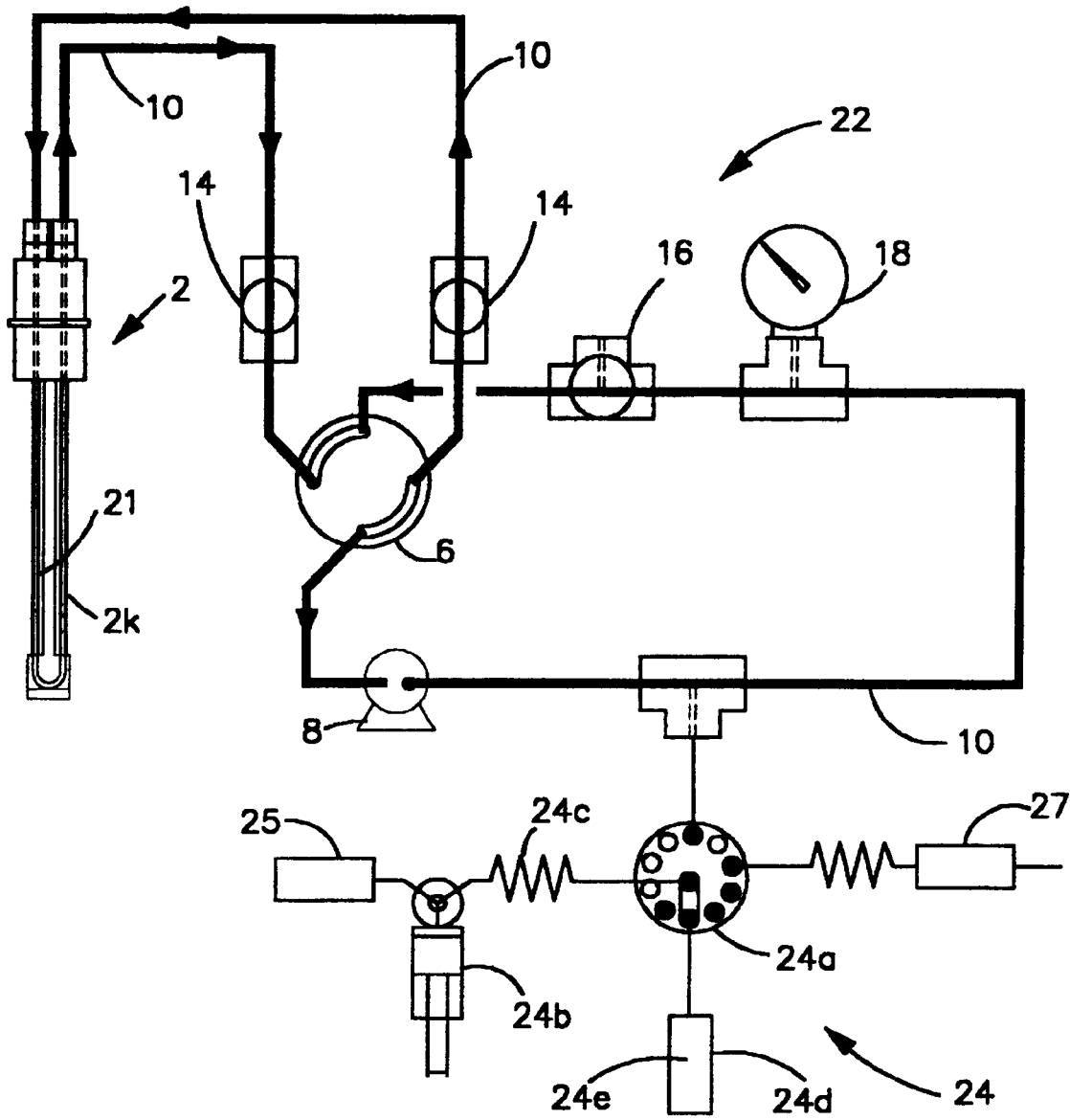
FIG. 4 is a schematic representation of a third embodiment of a sampling system utilizing the in-line filter probe shown in FIGS. 1-A and 1-B, made in accordance with the principles of the present invention.

Reference is now made to FIG. 4, in which is shown a third embodiment of a sampling system utilizing the in-line filter probe 2, made in accordance with the principles of the present invention and generally designated by the numeral 22. The configuration shown in FIG. 4 provides a second example of the application of the in-line filter probe 2 to analytical instrumentation. The sampling system 22 is identical to the sampling system 72 shown in FIG. 3, except that a sequential-injection analyzer 24 is utilized instead of the flow-injection analyzer 20a, and the means of sample takeoff are modified accordingly.

In this application, the necessary sample volume is extracted under suction by means of a downstream syringe pump and sequential-injection analyzer stream-selection valve. This application is particularly advantageous, as it adds the capability to automatically backwash the porous filter segments in addition to the normal manual backwash. The chemical backwash is accomplished by devoting one reagent channel of the sequential-injection analyzer (SIA) stream-selection valve 24a to the desired backwash chemical. Other channels connect to a carrier-solvent reservoir 25 and a detector 27. In addition, the SIA selection valve 24a is switched so that the SIA syringe pump 24b and holding coil 24 care connected to a backwash reagent reservoir 24d. Under suction of the syringe pump 24b, an aliquot/aliquant of the backwash reagent 24e is pulled through the selection valve 24a into the SIA holding coil 24c. The SIA stream-selection valve 24a is then actuated so that the syringe pump 24b and holding coil 24 care placed in fluid communication with the SIA selection-valve 24a port communicating with the in-line filter probe 2 and pump 8. This port is the same as that normally used for sample takeoff under syringe-pump action. Under syringe-pump pressure, the aliquot/aliquant of backwash reagent is pushed until it enters the unidirectional pumped flow path of the in-line filter probe 2. Then, under pressure from the sample circulation pump 8, the backwash chemical is pushed to and through the return porous filter segment 2k or 2l. As the chemical passes through the pores of the porous tubing 2k or 2l, the backwash chemical reagent dissolves and removes any wash-resistant particulate matter which might irreversibly block the pores, and which cannot be removed by a physical backwash. The chemical backwash just described is repeated after the stream-switching valve 6 has reversed the direction of fluid 10 flow, thereby chemically backwashing both filtration segments 2k and 2l. These chemical backwashes can be carried out under automatic computer control as frequently and as often as desired to obtain the desired or required degree of filter cleanup.

Figure 5:
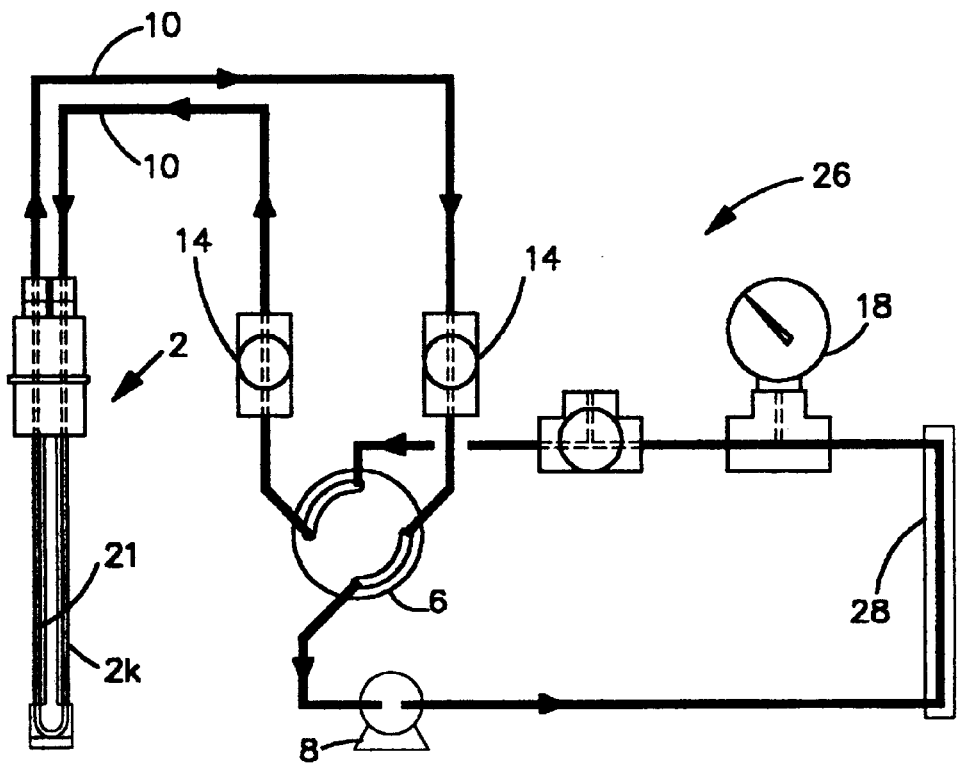
FIG. 5 is a schematic representation of a fourth embodiment of a sampling system utilizing the in-line filter probe shown in FIGS. 1-A and 1-B, made in accordance with the principles of the present invention.

Reference is now made to FIG. 5, in which is shown a fourth embodiment of a sampling system utilizing the in-line filter probe 2, made in accordance with the principles of the present invention and generally designated by the numeral 26. The sampling system 26 illustrates a third example of the use of the in-line filter probe 2 in combination with an analytical instrument; in this case, a spectrometer flow cell 28. As shown in FIG. 5, the spectrometer flow cell 28 is simply inserted into the unidirectional flow path of the filter probe 2, the only requirement being that the flow cell 28 be of sufficiently small internal volume as not to introduce significant washout lag time into the analytical cycle. If chemical backwash is desired, a dedicated syringe pump can be added. The inlet point for such a backwash capability would be downstream of the flow cell 28. The same considerations would apply to the sampling system 12 shown in FIG. 3, or to a similar system using a gas chromatograph (not shown) as the analytical instrument.

Figure 6:
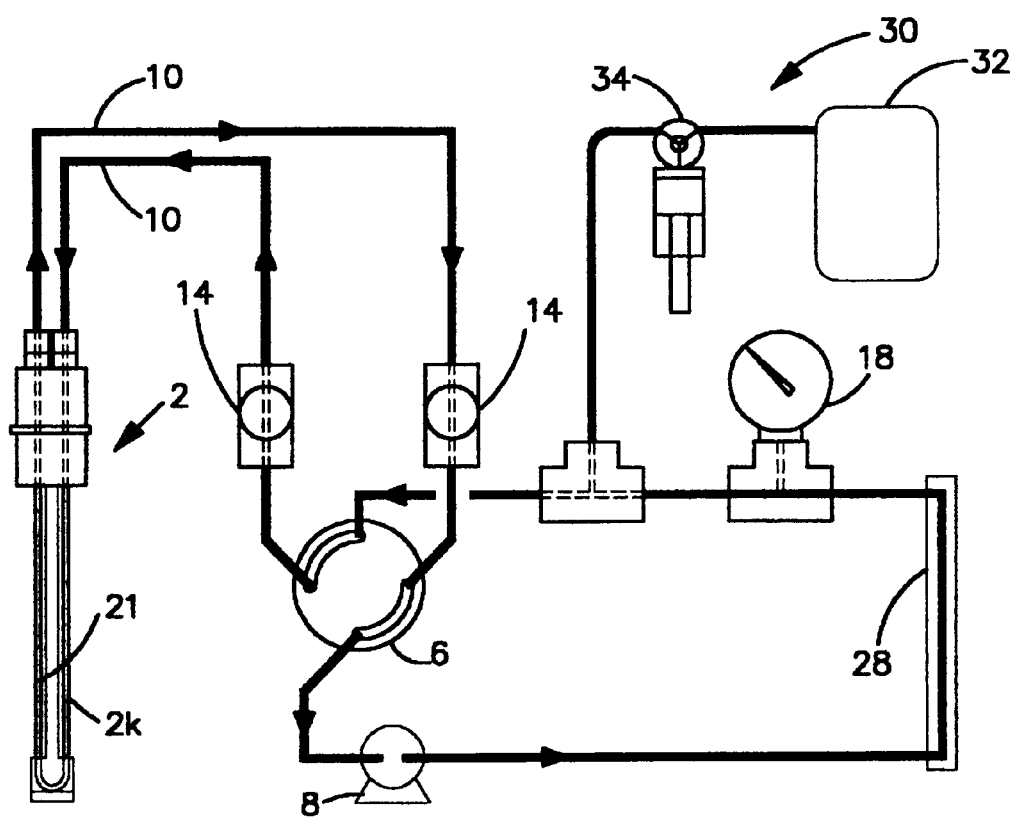
FIG. 6 is a schematic representation of a fifth embodiment of a sampling system utilizing the in-line filter probe shown in FIGS. 1-A and 1-B, made in accordance with the principles of the present invention.

Reference is now made to FIG. 6, which illustrates such a dedicated chemical backwash system, generally designated by the numeral 30. The system 30 comprises a container 32 of backwash reagent and a dedicated syringe pump 34.

All of the chemical/solvent cleaning means thus far described are intermittent in nature. For really difficult streams, it is possible to arrange for continuous chemical/solvent cleaning action in addition to continuous physical backwashing. In this arrangement a separate continuous pump replaces the syringe pump shown in FIG. 6, and the cleaning chemical is continuously pumped into the unidirectional flow loop.

It is important to note that the above means of physical and chemical do not require any interruption of clean sample flow to the analytical finish at any time (with the exception of the SIA application, where such stoppage of flow is inherent in sample extraction). Even in that case, however, flow continues uninterrupted through the sample bypass, so fresh sample is always available.

In addition to the advanced sample cleanup and filter-treatment capabilities provided by the present invention, the filter probe 2 provides the unique capability of being usable either in a flow cell remote from the sample point or inserted directly in a process vessel or piping.

Figure 7:
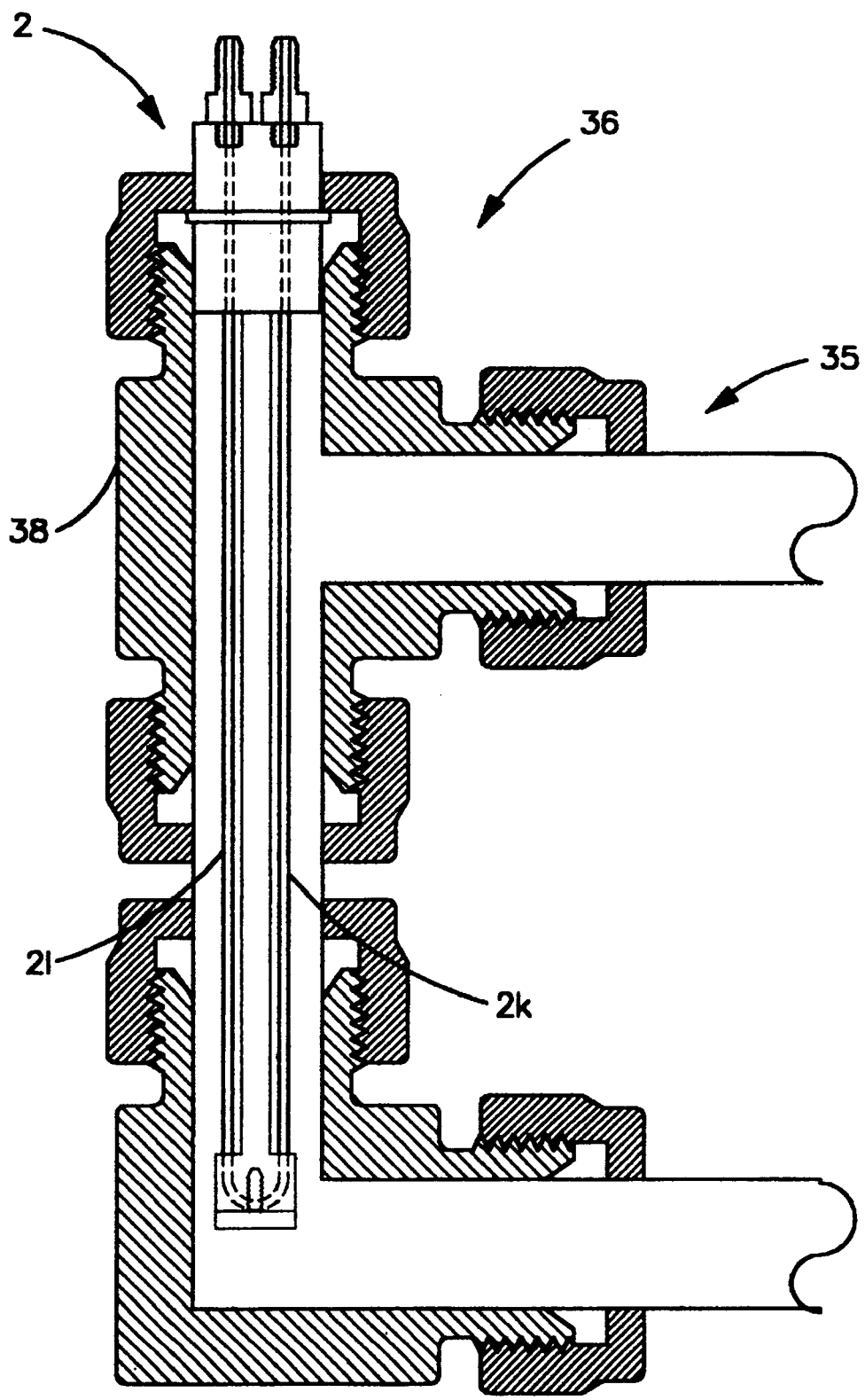
FIG. 7 is a schematic representation of a sampling system comprising the in-line filter probe disposed in a flow cell, in accordance with the principles of the present invention.

Reference is now made to FIG. 7, in which is shown a sampling system utilizing the filter probe 2 disposed in a process flow cell 35, the sampling system being generally designated by the numeral 36. The filter probe 2 is small enough to fit easily inside one-inch pipe or tubing 38, thereby permitting the filter probe 2 to fit easily into a flow cell 35 constructed of one-inch tube fittings (Swagelok® style). The flow cell 35 is typically mounted at the analyzer house, and raw sample circulated to and through the flow cell 35 by process pressure or a dedicated pump.

Figure 8:
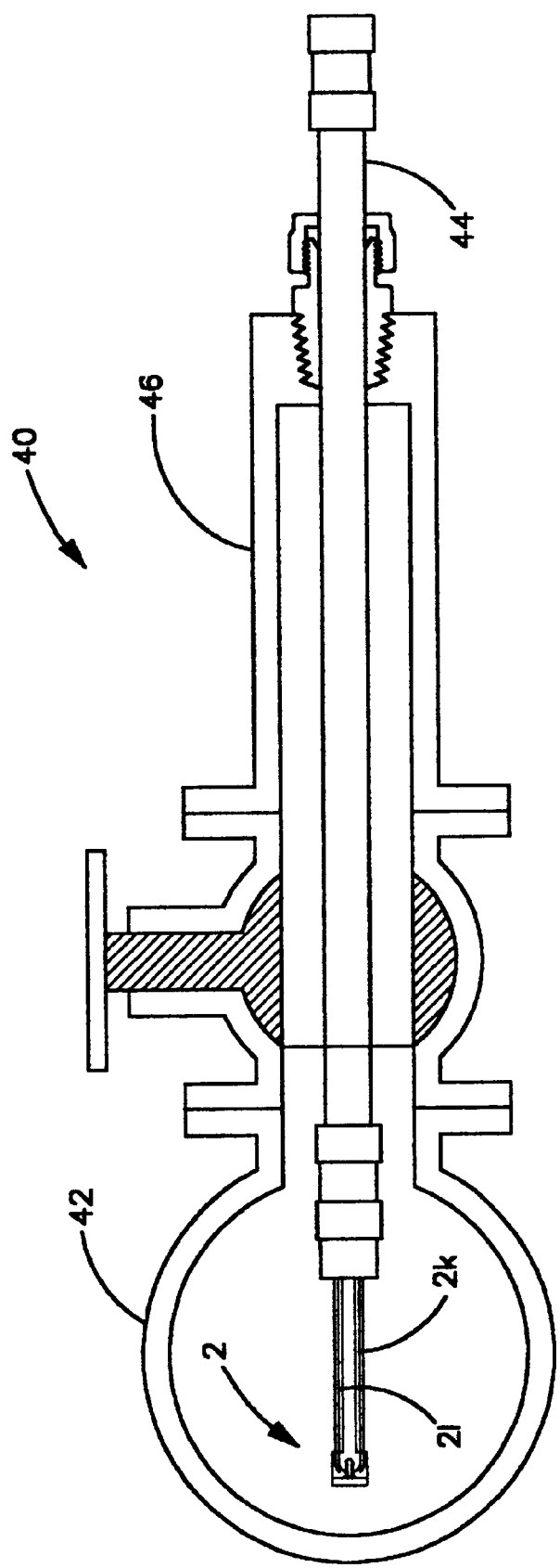
FIG. 8 is a schematic representation of a sampling system comprising the in-line filter probe installed in a containment vessel, in accordance with the principles of the present invention.

Reference is now made to FIG. 8, in which is shown the filter probe 2 installed in pipe or vessel 42, the sampling system being generally designated by the numeral 40. Since the connector ends of the in-line filter probe 2 are designed to socket into a one-inch tube size (Swagelok® type) fitting, the probe 2 can be installed in such a one-inch union at the end of a long length 44 of one-inch tubing. This long length 44 of one-inch tubing can be further placed in a lock chamber 46 arrangement that will allow easy insertion into and removal from large-diameter process piping 42, without need to shut process flow off for such insertion or removal.

Such a probe configuration can be inserted directly into tanks 42 and other such vessels. All that is required is a sufficient length of one-inch tube/pipe and interconnecting tubing from the two filter elements to the filter probe's 2 switching valve and circulating pump. In such installations it is envisioned that the backwash valve and circulating pump would be mounted as close to the tank/pipe as practicable, with the unidirectional-flow portion of the probe's 2 circulation loop flowing to the location of the analytical finish.

In summary, the in-line filter probe 2 assembly provides maximally reliable sampling for automated process analysis. It consumes/removes and treats the absolute minimum sample required for analysis, in most cases removing only a few microliters per analytical cycle, and in some special cases removing no material permanently from the process. The filter probe 2 is especially suitable for small-volume reactors. It provides the capability to both physically and chemically automatically remove filter-plugging materials from the probe 2. The compact size and unitary construction of the probe 2 facilitate ease of insertion into and removal from the process for any additional maintenance and/or replacement. It provides means of continuously physically back flushing the filter element using filtered sample solution while simultaneously providing filtered sample. Prior-art filters tangentially flush, using unfiltered sample solution, and thus do not address completely the problem of blocked pores. Some systems periodically blow back to dislodge cake, using either the sample or even compressed air, but no sampling can take place while this is in progress. It provides a means of introducing an additional intermittent or even continuous chemical/solvent wash solution. Because the system provides a means of simultaneous back flushing and filtration, washing and filtering can be done concurrently and continuously (or-intermittently) without interrupting the flow of filtered sample. It can be made self-maintaining by using pressure or flow set points to trigger the switching valve, operated on a time-based control scheme or controlled by either an instrument or a plant computer.

I claim:

1. A sampling system for process analysis utilizing an in-line filter probe, the system comprising:

(a) a support element; and (b) a U-shaped porous tube mounted on the support element, the U-shaped porous tube comprising a first segment having an open first end and a closed second end, and a second segment having an open first end and a closed second end, the second ends of the first and second segments being closed and connected to one another by a sealed third segment.

2. The sampling system of claim 1, wherein the third segment of the porous tube is sealed by compression.

3. A method for obtaining samples for process analysis utilizing an in-line filter probe, the method comprising the steps of:

(a) providing an in-line filter probe comprising a support element and a U-shaped porous tube mounted on the support element, the U-shaped porous tube comprising a first segment having an open first end and a closed second end, and a second segment having an open first end and a closed second end, the second ends of the first and second segments being closed and connected to one another by a sealed third segment;

(b) disposing the filter probe in a fluid to be sampled; and (c) circulating the fluid through the porous tube.

4. The method of claim 3, wherein the third segment of the porous tube is sealed by compression.

* * * * *